(12) United States Patent
Chavatte et al.

(10) Patent No.: US 8,911,497 B2
(45) Date of Patent: Dec. 16, 2014

(54) MINIMALLY INVASIVE SPINE AUGMENTATION AND STABILIZATION SYSTEM AND METHOD

(75) Inventors: Kris Chavatte, Kuesnacht (CH); Markus Weber, Jegenstorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 671 days.

(21) Appl. No.: 12/755,256

(22) Filed: Apr. 6, 2010

(65) Prior Publication Data
US 2010/0262242 A1   Oct. 14, 2010

Related U.S. Application Data

(60) Provisional application No. 61/168,046, filed on Apr. 9, 2009.

(51) Int. Cl.
| | | |
|---|---|---|
| *A61F 2/44* | (2006.01) | |
| *A61B 17/70* | (2006.01) | |
| *A61B 19/00* | (2006.01) | |
| *A61B 17/34* | (2006.01) | |

(52) U.S. Cl.
CPC ....... *A61B 17/7098* (2013.01); *A61B 2019/307* (2013.01); *A61B 17/7097* (2013.01); *A61B 2019/5437* (2013.01); *A61B 17/3472* (2013.01)
USPC ............... 623/17.12; 623/17.11; 606/246; 606/279; 606/92; 606/105

(58) Field of Classification Search
USPC .............. 606/246, 279, 92–94, 105; 623/17.11–17.13, 17.15, 17.16
See application file for complete search history.

(56) References Cited

U.S. PATENT DOCUMENTS

| | | |
|---|---|---|
| 2,381,050 A | 12/1943 | Hardinge |
| 3,701,703 A | 10/1972 | Zimmer et al. |
| 3,867,728 A | 2/1975 | Stubstad et al. |

(Continued)

FOREIGN PATENT DOCUMENTS

| | | |
|---|---|---|
| EP | 0 493 789 | 12/1991 |
| EP | 0 872 257 | 10/1998 |

(Continued)

OTHER PUBLICATIONS

Jensen, Mary E., et al., "Percutaneous Polymethylmethacrylate Vertebroplasty in the Treatment of Osteoporotic Vertebral Body Compression Fractures: Technical Aspects"., AJNR: 18, Nov. 1997.

(Continued)

*Primary Examiner* — Andrew Yang
*Assistant Examiner* — Olivia C Chang
(74) *Attorney, Agent, or Firm* — Baker & Hostetler LLP

(57) ABSTRACT

A minimally invasive system and method for vertebral body augmentation includes an expandable containment device, a chassis including an interior cavity for at least partially enclosing the expandable containment device, a first guidewire, a working cannula, a second guidewire having at least a partially flexible distal end portion and a sleeve for introducing bone filler material through a cannulated passageway of the sleeve and into an interior cavity of the containment device. The containment device preferably includes a plurality of pores for directing the outflow of bone filler material anteriorly within the vertebral body. The containment device and chassis are left interior to the vertebral body subsequent to height restoration and augmentation of the vertebral body.

27 Claims, 13 Drawing Sheets

(56) References Cited

U.S. PATENT DOCUMENTS

| | | | |
|---|---|---|---|
| 4,055,029 A | 10/1977 | Kalbow st al. |
| 4,327,736 A | 5/1982 | Inoue |
| 4,364,392 A | 12/1982 | Strother et al. |
| 4,735,625 A | 4/1988 | Davidson |
| 4,755,184 A | 7/1988 | Silverberg |
| 4,820,349 A | 4/1989 | Saab |
| 4,969,888 A | 11/1990 | Scholten et al. |
| 4,986,830 A | 1/1991 | Owens et al. |
| 5,041,114 A | 8/1991 | Chapman et al. |
| 5,049,132 A | 9/1991 | Shaffer et al. |
| 5,059,193 A | 10/1991 | Kuslich |
| 5,098,381 A | 3/1992 | Schneider |
| 5,108,404 A | 4/1992 | Scholten et al. |
| 5,192,326 A | 3/1993 | Bao et al. |
| 5,352,199 A | 10/1994 | Tower |
| 5,390,683 A | 2/1995 | Pisharodi |
| 5,443,496 A | 8/1995 | Schwartz et al. |
| 5,549,679 A | 8/1996 | Kuslich |
| 5,571,189 A | 11/1996 | Kuslich |
| 5,599,301 A | 2/1997 | Jacobs et al. |
| 5,601,593 A | 2/1997 | Freitag |
| 5,674,295 A | 10/1997 | Ray et al. |
| 5,693,100 A | 12/1997 | Pisharodi |
| 5,707,390 A | 1/1998 | Bonutti |
| 5,759,191 A | 6/1998 | Barbere |
| 5,800,392 A | 9/1998 | Racchini |
| 5,827,289 A | 10/1998 | Reiley et al. |
| 5,893,850 A | 4/1999 | Cachia |
| 5,972,015 A | 10/1999 | Scribner et al. |
| 6,096,038 A | 8/2000 | Michelson |
| 6,127,597 A | 10/2000 | Beyar et al. |
| 6,179,856 B1 | 1/2001 | Barbere |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,306,177 B1 | 10/2001 | Felt et al. |
| 6,395,032 B1 | 5/2002 | Gauchet |
| 6,402,784 B1 | 6/2002 | Wardlaw |
| 6,423,083 B2 | 7/2002 | Reiley et al. |
| 6,440,138 B1 | 8/2002 | Reiley et al. |
| 6,478,800 B1 | 11/2002 | Fraser et al. |
| 6,558,390 B2 | 5/2003 | Cragg |
| 6,565,606 B1 | 5/2003 | Bruce et al. |
| 6,613,054 B2 | 9/2003 | Scribner et al. |
| 6,620,162 B2 | 9/2003 | Kuslich et al. |
| 6,632,235 B2 | 10/2003 | Weikel et al. |
| 6,638,246 B1 | 10/2003 | Naimark et al. |
| 6,663,647 B2 | 12/2003 | Reiley et al. |
| 6,679,886 B2 | 1/2004 | Weikel et al. |
| 6,706,069 B2 | 3/2004 | Berger |
| 6,716,216 B1 | 4/2004 | Boucher et al. |
| 6,719,761 B1 | 4/2004 | Reiley et al. |
| 6,719,773 B1 | 4/2004 | Boucher et al. | 606/192 |
| 6,726,691 B2 | 4/2004 | Osorio et al. |
| 6,733,532 B1 | 5/2004 | Gauchet et al. |
| 6,740,093 B2 | 5/2004 | Hochschuler et al. |
| 6,852,095 B1 | 2/2005 | Ray |
| 6,863,672 B2 | 3/2005 | Reiley et al. |
| 6,899,719 B2 | 5/2005 | Reiley et al. |
| 6,969,404 B2 | 11/2005 | Ferree |
| 6,981,981 B2 | 1/2006 | Reiley et al. |
| 7,001,431 B2 | 2/2006 | Bao et al. |
| 7,011,684 B2 | 3/2006 | Eckman |
| 7,025,771 B2 | 4/2006 | Kuslich et al. |
| 7,044,954 B2 | 5/2006 | Reiley et al. |
| 7,097,648 B1 | 8/2006 | Globerman et al. |
| 7,153,307 B2 | 12/2006 | Scribner et al. |
| 7,166,121 B2 | 1/2007 | Reiley et al. |
| 7,175,627 B2 | 2/2007 | Lin et al. |
| 7,175,628 B2 | 2/2007 | Lin et al. |
| 7,175,629 B2 | 2/2007 | Lin et al. |
| 7,226,481 B2 | 6/2007 | Kuslich |
| 7,241,303 B2 | 7/2007 | Reiss et al. |
| 7,261,720 B2 | 8/2007 | Stevens et al. |
| 2002/0058947 A1 | 5/2002 | Hochschuler et al. |
| 2002/0068974 A1 | 6/2002 | Kuslich et al. |
| 2003/0220649 A1 | 11/2003 | Bao et al. |
| 2004/0073308 A1 | 4/2004 | Kuslich et al. |
| 2004/0097930 A1 | 5/2004 | Justis et al. |
| 2004/0098017 A1 | 5/2004 | Saab et al. |
| 2004/0102774 A1 | 5/2004 | Trieu |
| 2004/0167625 A1 | 8/2004 | Beyar et al. |
| 2004/0210297 A1 | 10/2004 | Lin et al. |
| 2004/0215343 A1 | 10/2004 | Hochschuler et al. |
| 2004/0215344 A1 | 10/2004 | Hochschuler et al. |
| 2004/0220615 A1 | 11/2004 | Lin et al. |
| 2005/0010297 A1 | 1/2005 | Watson et al. |
| 2005/0070911 A1 | 3/2005 | Carrison et al. |
| 2005/0143827 A1 | 6/2005 | Globerman et al. |
| 2005/0209595 A1 | 9/2005 | Karmon |
| 2005/0209629 A1 | 9/2005 | Kerr et al. |
| 2005/0234498 A1 | 10/2005 | Gronemeyer et al. |
| 2005/0273049 A1 | 12/2005 | Krulevitch et al. |
| 2006/0009844 A1 | 1/2006 | Bloemer et al. |
| 2006/0079905 A1 | 4/2006 | Beyar et al. |
| 2006/0100706 A1 | 5/2006 | Shadduck et al. |
| 2006/0106459 A1 | 5/2006 | Truckai et al. |
| 2006/0149379 A1 | 7/2006 | Kuslich et al. |
| 2006/0155296 A1 | 7/2006 | Richter |
| 2006/0173464 A1 | 8/2006 | Ellman et al. |
| 2006/0182780 A1 | 8/2006 | Riley et al. |
| 2006/0190083 A1 | 8/2006 | Arnin et al. |
| 2006/0217736 A1 | 9/2006 | Kaneko et al. |
| 2006/0229625 A1 | 10/2006 | Truckai et al. |
| 2006/0235425 A1 | 10/2006 | Lin et al. |
| 2006/0271061 A1 | 11/2006 | Beyar et al. |
| 2006/0293750 A1 | 12/2006 | Sherman et al. |
| 2007/0055266 A1 | 3/2007 | Osorio et al. |
| 2007/0055267 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio et al. |
| 2007/0118142 A1 | 5/2007 | Krueger et al. |
| 2007/0156251 A1 | 7/2007 | Karmon |
| 2007/0168031 A1 | 7/2007 | Hudgins et al. |
| 2007/0213760 A1 | 9/2007 | Hayes et al. |
| 2007/0219490 A1 | 9/2007 | Pepper et al. |
| 2007/0233258 A1 | 10/2007 | Hestad et al. |
| 2007/0282443 A1 | 12/2007 | Globerman et al. |
| 2008/0009828 A1* | 1/2008 | Miller et al. | 604/509 |
| 2008/0027546 A1 | 1/2008 | Semler et al. |
| 2008/0086133 A1 | 4/2008 | Kuslich et al. |
| 2008/0300687 A1* | 12/2008 | Lin et al. | 623/17.12 |
| 2009/0030468 A1 | 1/2009 | Sennett et al. | 606/86 |
| 2009/0069850 A1 | 3/2009 | Fuerderer |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu et al. |
| 2009/0131950 A1 | 5/2009 | Liu et al. |
| 2009/0182427 A1 | 7/2009 | Liu et al. |
| 2009/0299282 A1 | 12/2009 | Lau et al. |
| 2009/0326538 A1 | 12/2009 | Sennett et al. |
| 2010/0168858 A1* | 7/2010 | Hardenbrook et al. | 623/17.12 |

FOREIGN PATENT DOCUMENTS

| | | |
|---|---|---|
| JP | 2002-531229 A | 9/2002 |
| JP | 2004-248791 A | 9/2004 |
| JP | 2006-522612 A | 10/2006 |
| WO | WO 95/05209 | 2/1995 |
| WO | WO 96/04952 | 2/1996 |
| WO | WO 98/56301 | 12/1998 |
| WO | WO 00/33909 A1 | 6/2000 |
| WO | WO 01/76514 | 10/2001 |
| WO | WO 02/43628 | 6/2002 |
| WO | WO 03/007853 | 1/2003 |
| WO | WO 2004/043271 A1 | 5/2004 |
| WO | WO 2005/048856 | 6/2005 |
| WO | WO 2006/034396 | 3/2006 |

(56) References Cited

FOREIGN PATENT DOCUMENTS

WO   WO 2008/097659 A2   8/2008
WO   WO 2009/064847      5/2009

OTHER PUBLICATIONS

Gangi, Afshin, et al., "Percutaneous Vertebroplasty Guided by a Combination of CT and Fluoroscopy"., AJNR 15:83-86, Jan. 1994.

Cotten, Anne., MD., et al. "Percutaneous Vertebroplasty for Osteolytic Metastases and Myeloma: Effects of the Percentage of Lesion Filling and the Leakage of Methyl Methacrylate at Clinical Follow-up"., Radiology 1996; 200:525-530.

Cotten, Anne, et al., "Preoperative Percutaneous Injection of Methyl Methacrylate and N-Butyl Cyanoacrylate in Vertebral Hemangiomas"; AJNR 17:137-142 (1996).

Maciunas, Robert J., MD., "Endovascular Neurological Intervention"; American Association of Neurological Surgeons; 153-158.

Microporous PTA balloon catheter; Schneider (Europe) AG.

* cited by examiner

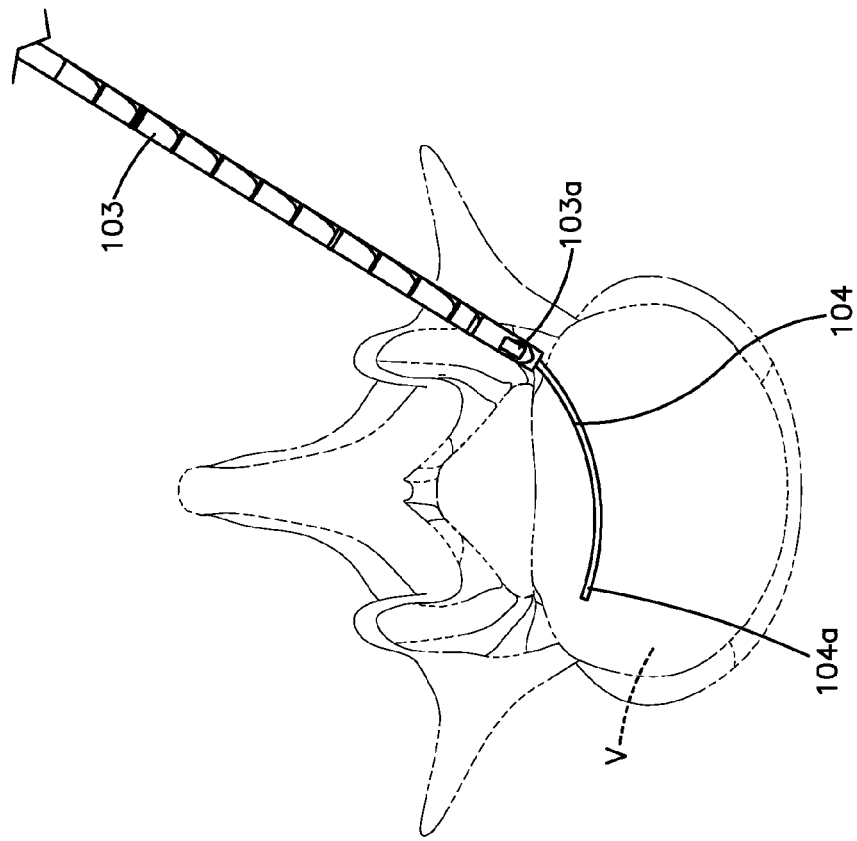
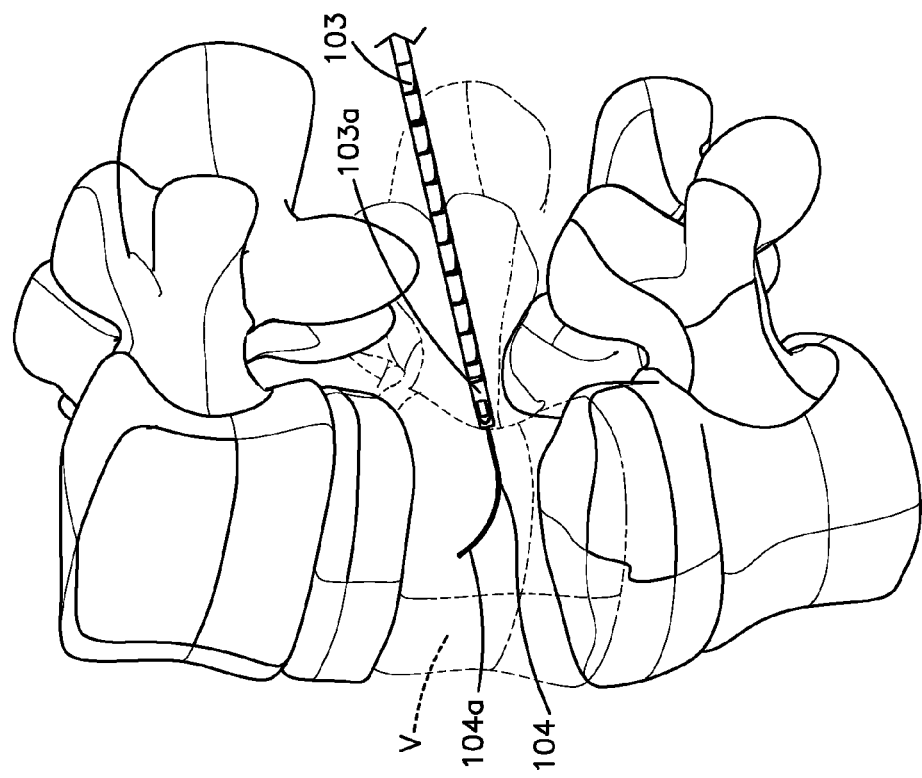

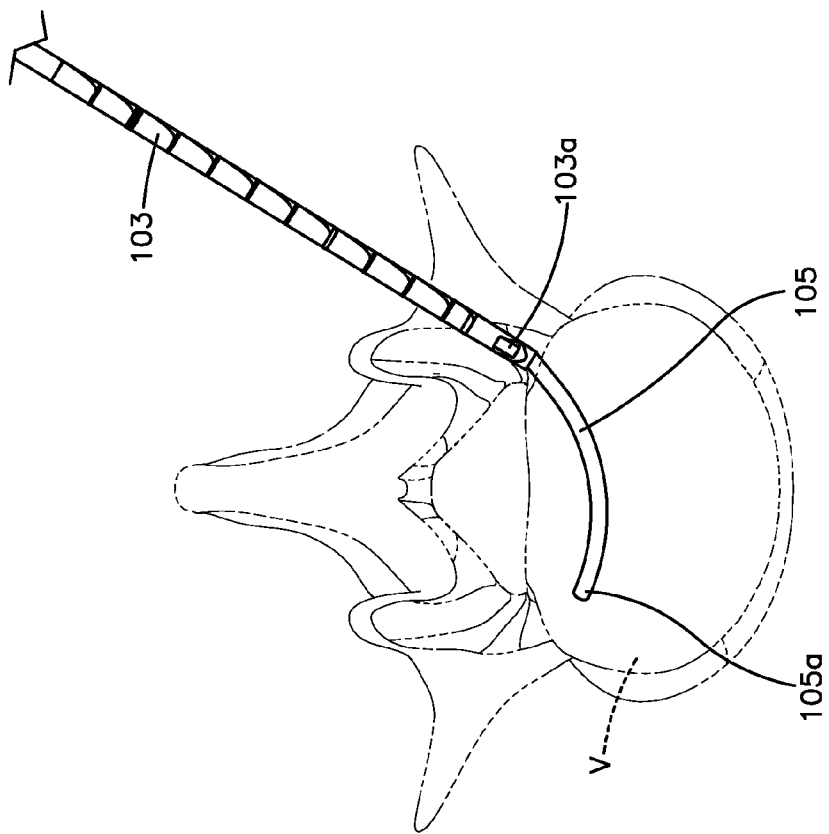
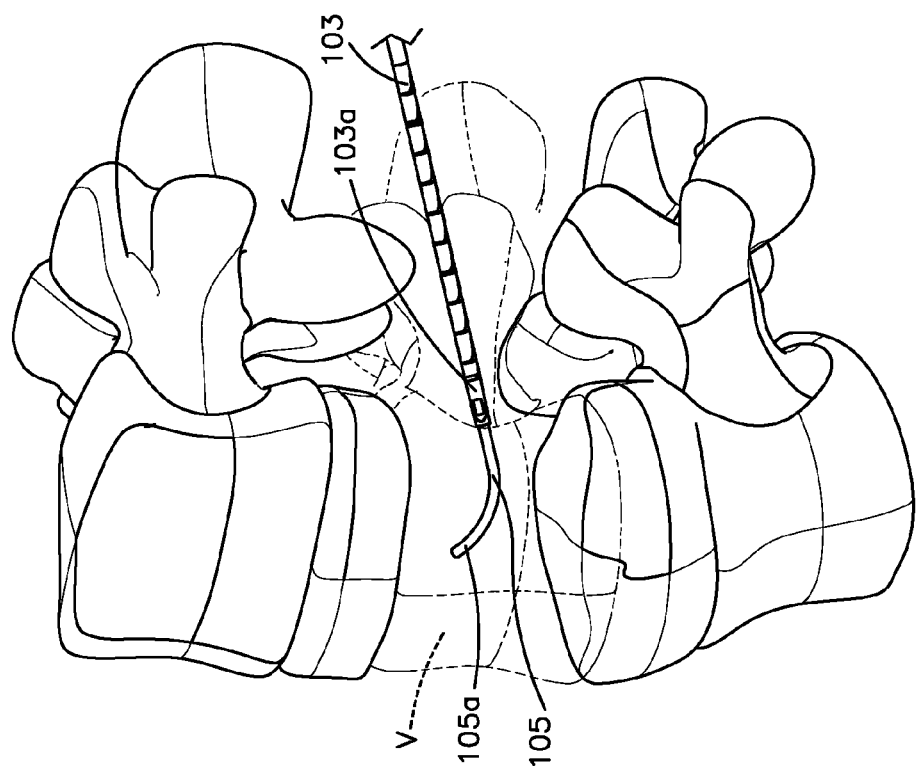

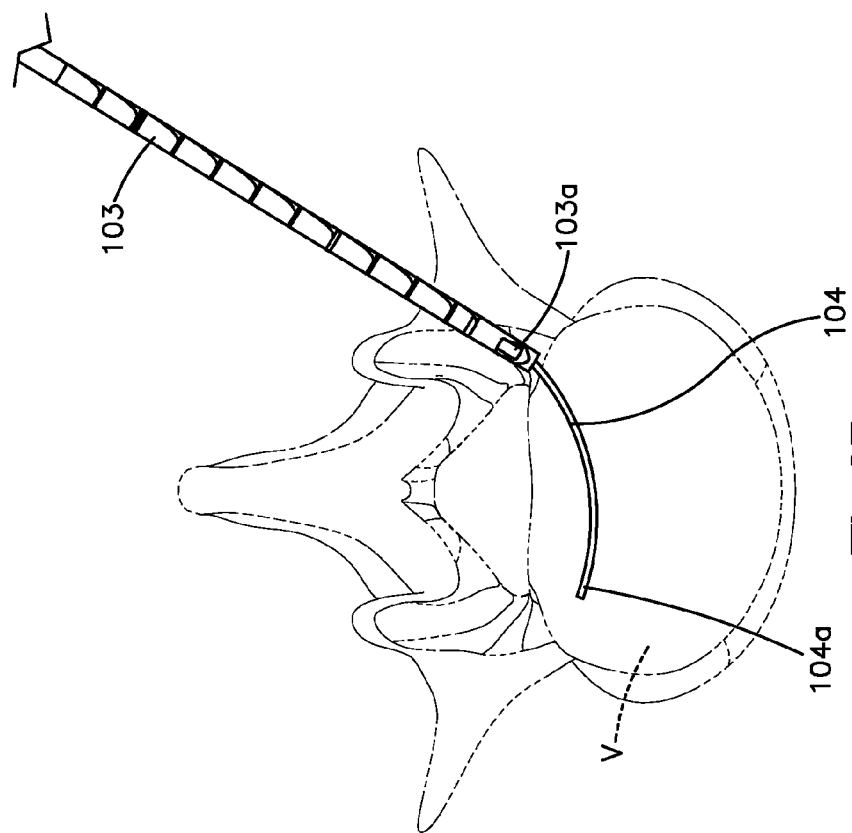
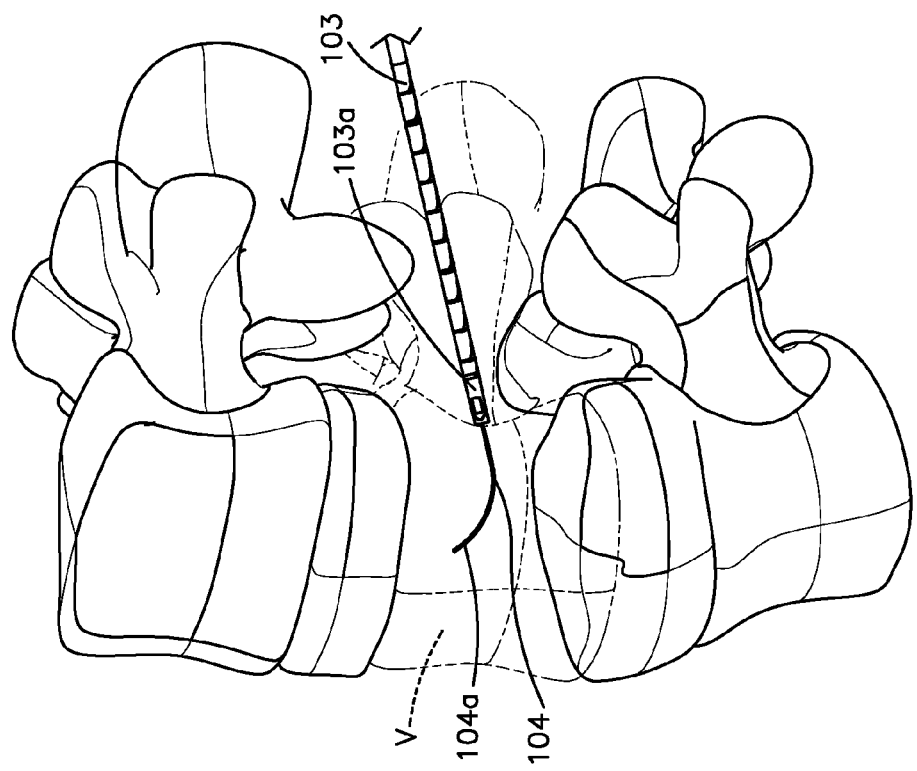

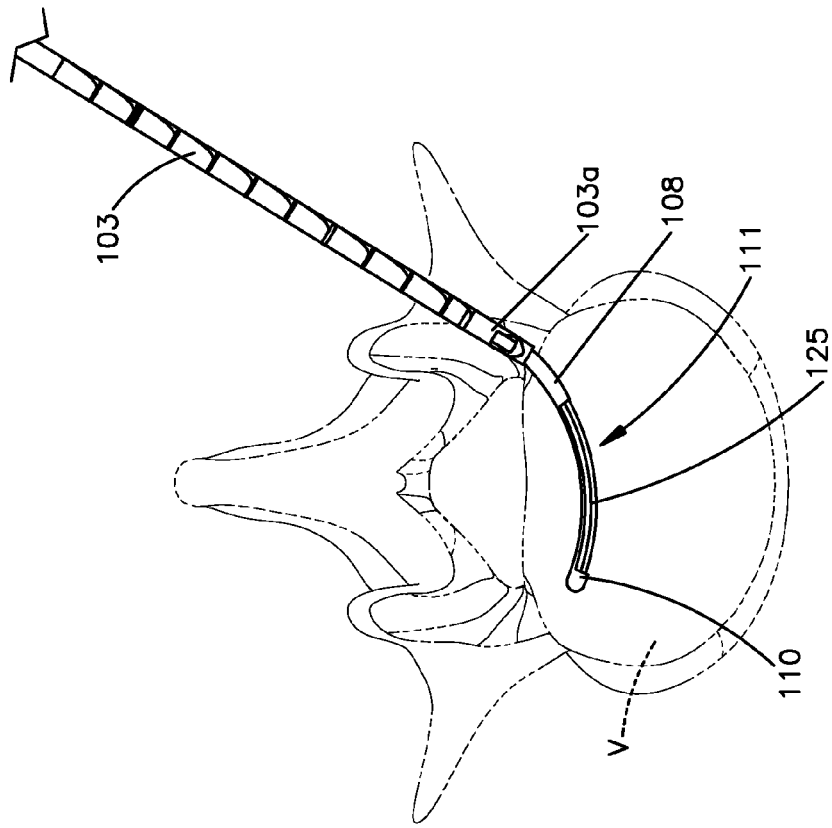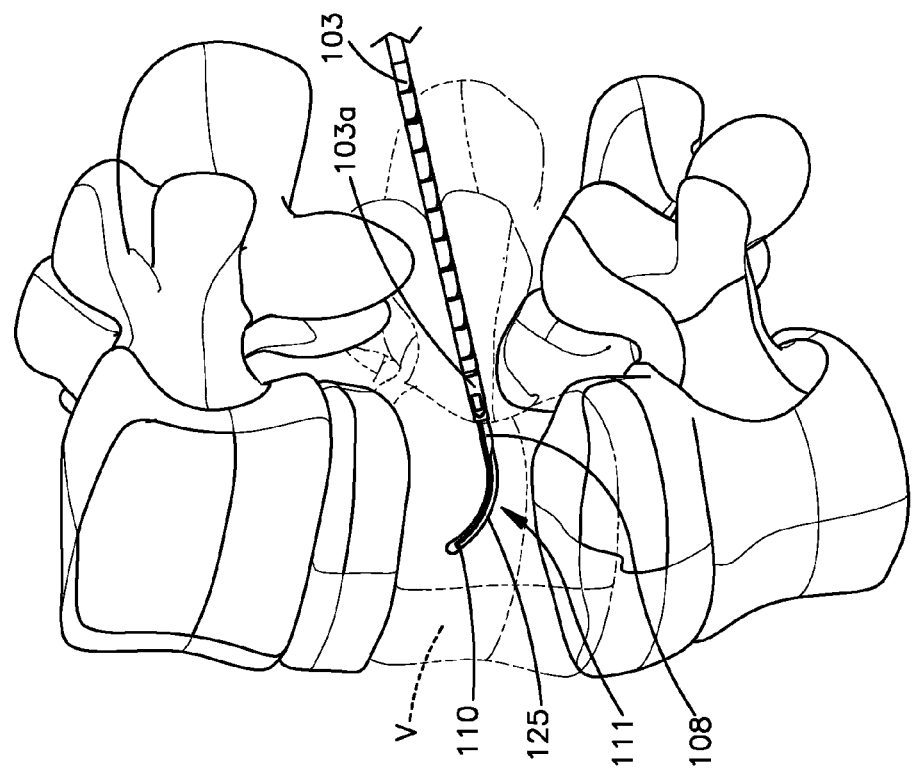

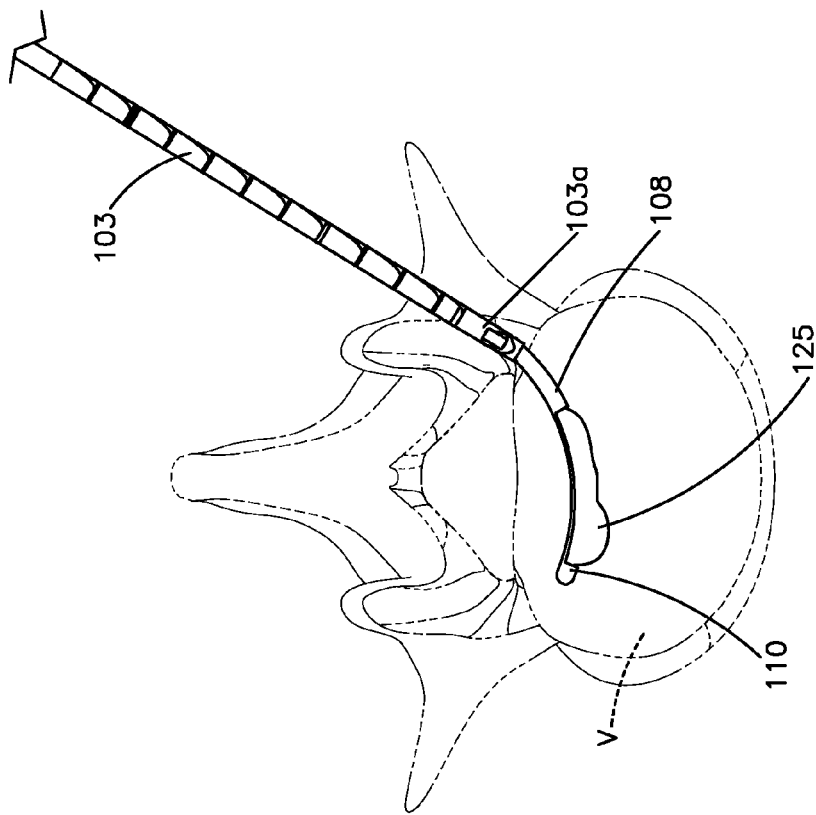
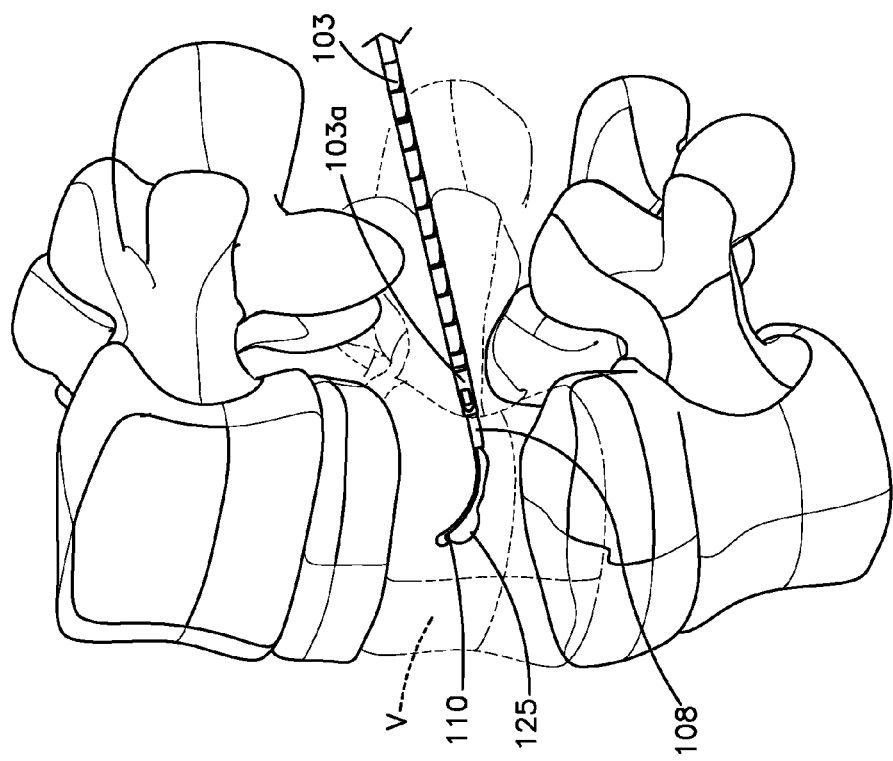

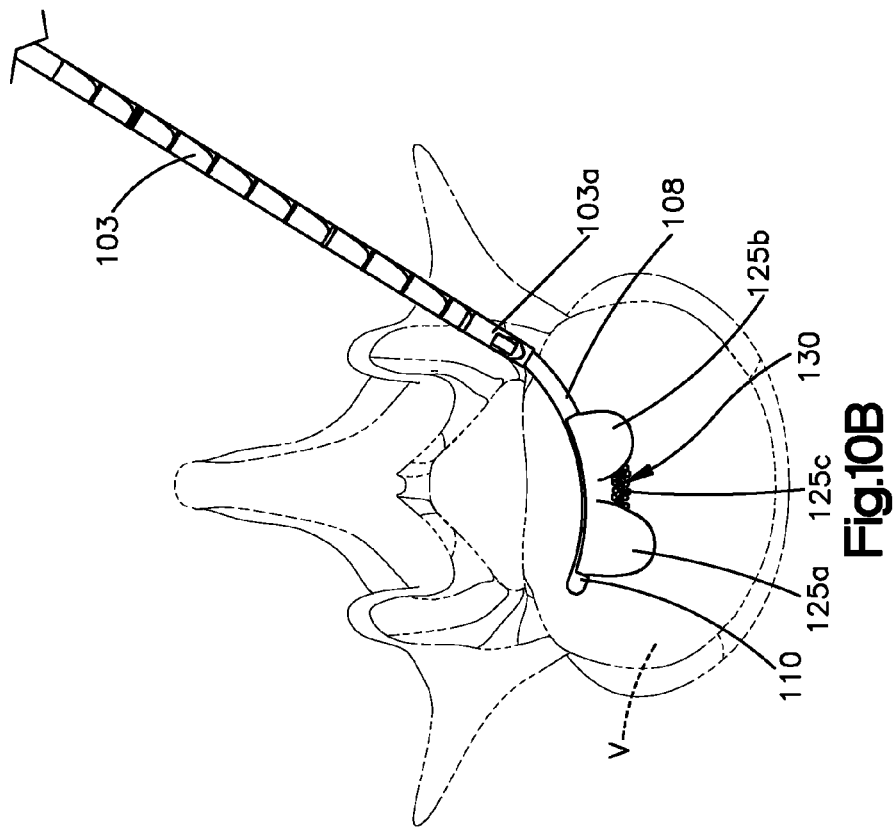
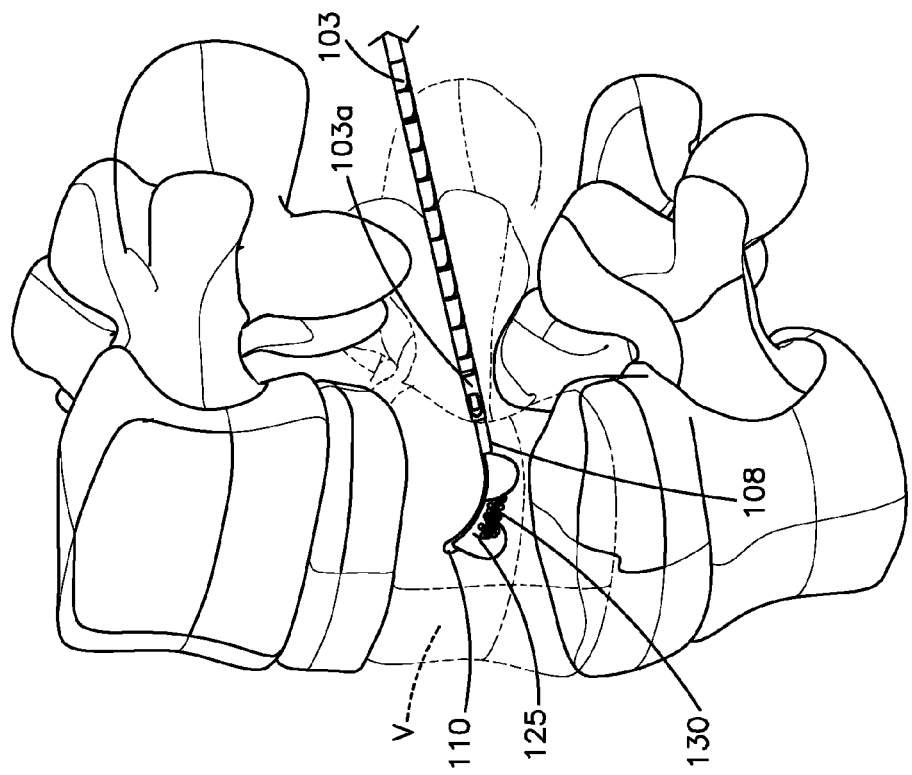

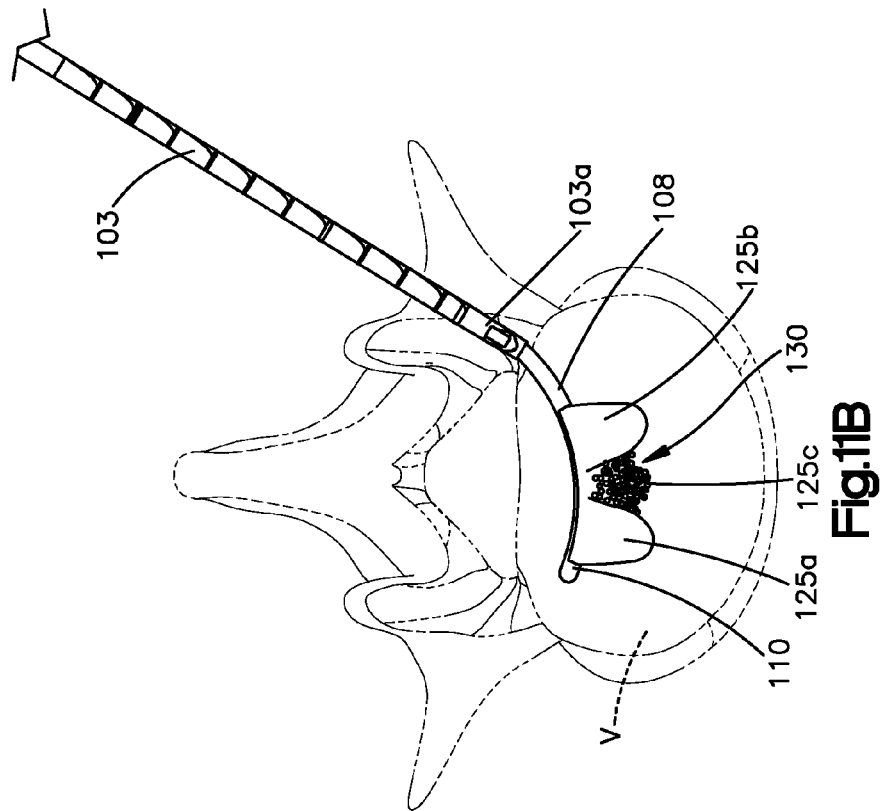
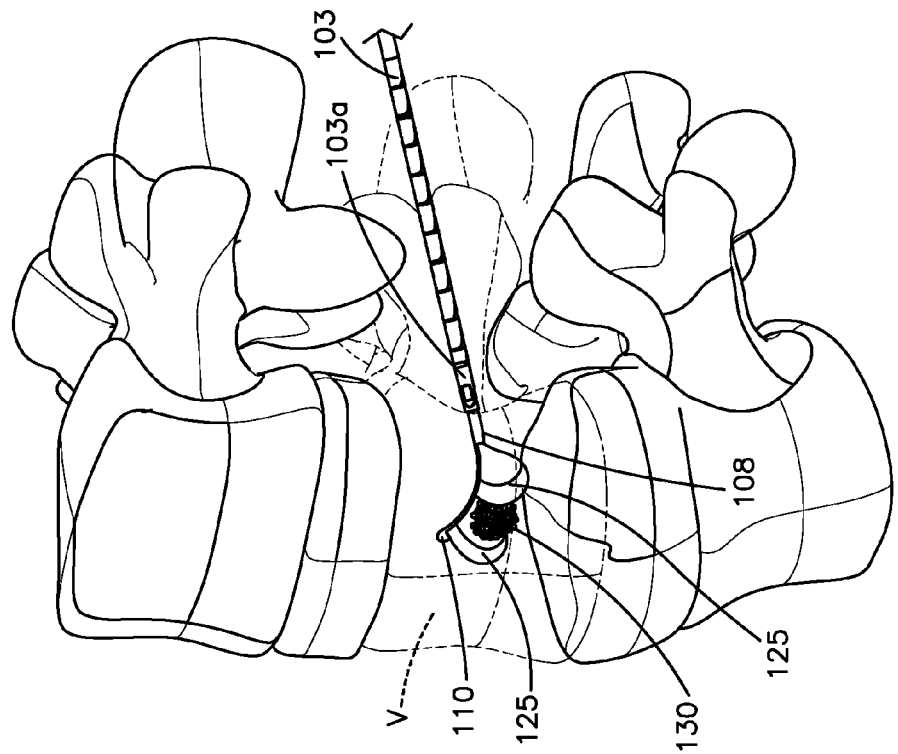

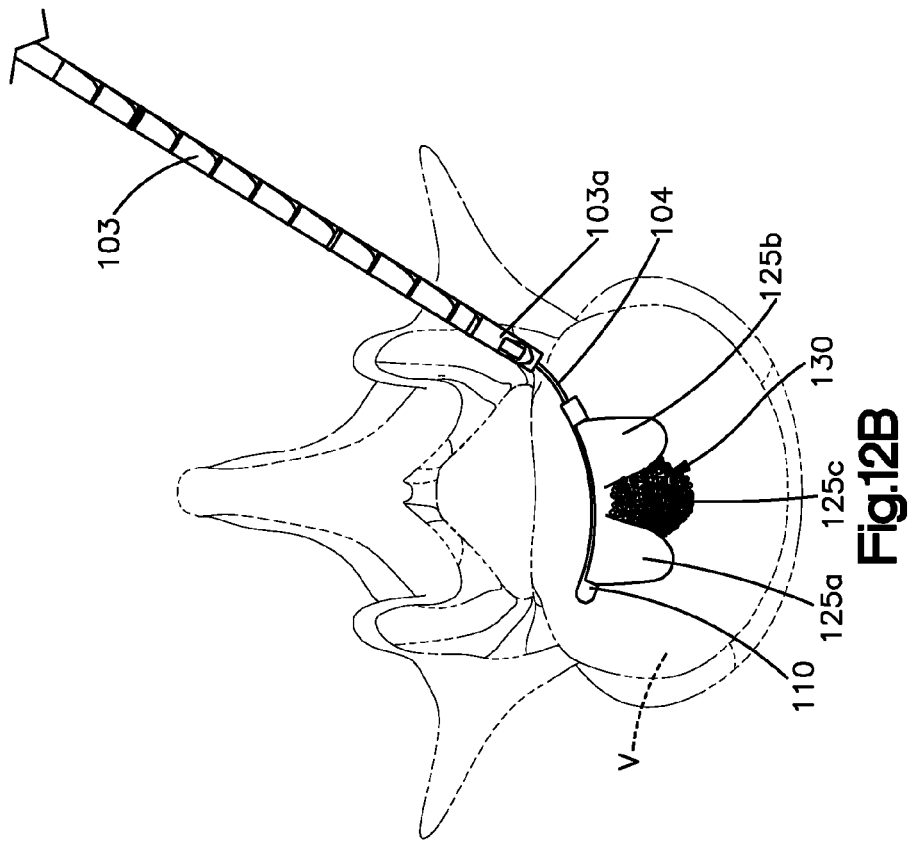
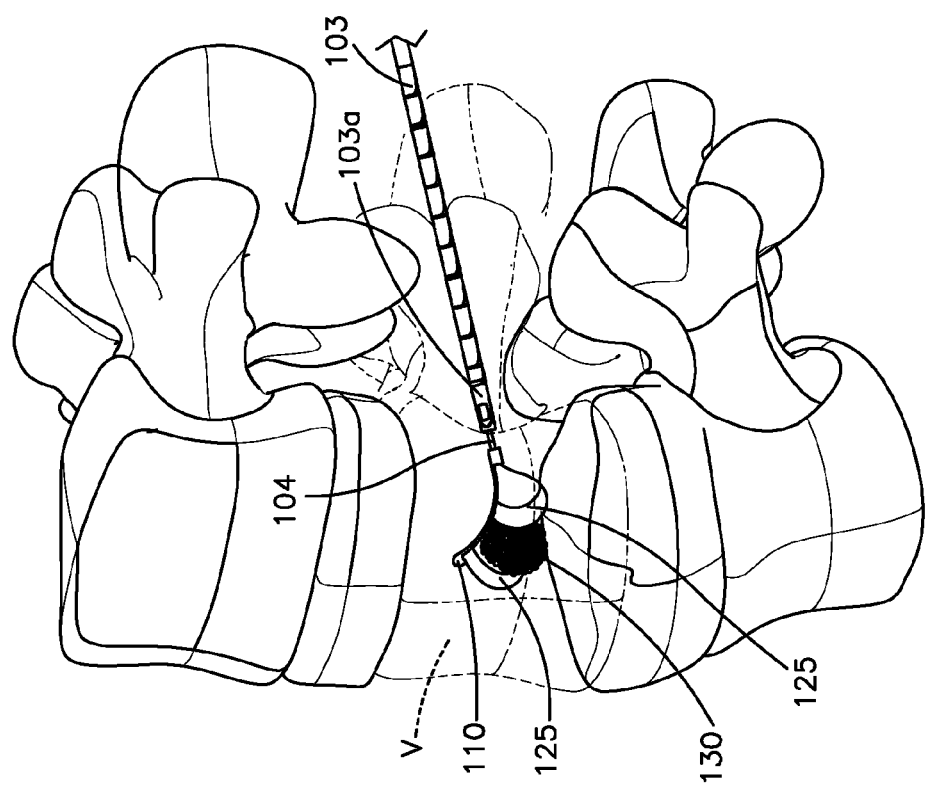

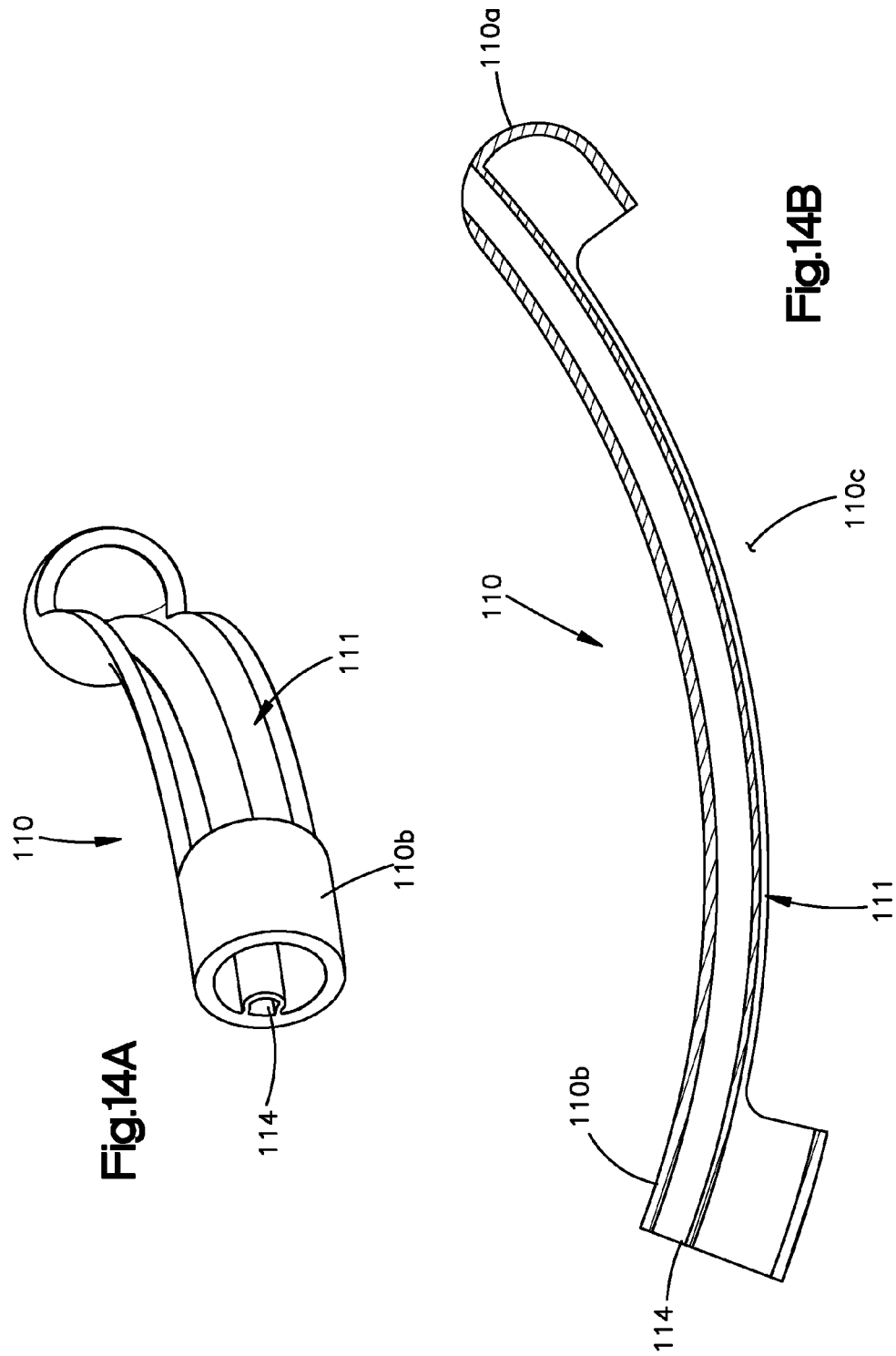

MINIMALLY INVASIVE SPINE AUGMENTATION AND STABILIZATION SYSTEM AND METHOD

CROSS REFERENCE TO RELATED APPLICATIONS

This application claims the benefit of U.S. Provisional Application No. 61/168,046, filed on Apr. 9, 2009, titled "Minimally Invasive Spine Augmentation and Stabilization System and Method," the contents of which is hereby incorporated by reference in its entirety.

BACKGROUND OF THE INVENTION

Vertebral compression fractures ("VCF") represent a spinal injury and may result in prolonged disability. Generally, VCF involves the collapse of one or more vertebral bodies in the spine. VCF usually occurs in the lower vertebrae of the thoracic spine or the upper vertebrae of the lumbar spine. The anterior portion of the vertebral body is typically collapsed to a further extent than a posterior portion, resulting in a potentially wedge-shaped, compressed vertebral body, during a VCF event. VCF may result in deformation of the normal alignment or curvature, e.g., lordosis, of the vertebral bodies in the affected area of the spine. VCF and/or related spinal deformities may initiate from, for example, metastatic diseases of the spine, trauma and/or osteoporosis. Until recently, doctors were limited in their treatment options for VCF and related spinal deformities.

Minimally invasive surgical procedures for treating VCF have been developed. A cannula or other access tools are typically inserted through the posterior of the targeted vertebral body, usually through the pedicles in such procedures. For example, U.S. Published Patent Application No. 2009-0069850 describes a balloon with an implant mounted thereon that is insertable through a posterior duct into a compressed vertebral body and expanded to urge endplates of the vertebral body toward an original spacing or shape.

In another such procedure, generally referred to as vertebralplasty, a cannula or bone needle is passed through the soft tissue of the patient's back. Once positioned within the compressed vertebral body, a small amount of polymethylmethacrylate (PMMA) or other orthopedic bone cement is pushed through the needle into the targeted vertebral body. This technique may be effective in the reduction or elimination of fracture pain, prevention of further collapse, and a return to mobility in patients. However, this technique typically does not reposition the fractured bone into its original size and/or shape and, therefore, may not address the problem of spinal deformity due to the fracture.

Other treatments for VCF generally involve two phases including (1) reposition or restoration of the original height of the vertebral body and consequent lordotic correction of the spinal curvature; and (2) augmentation or addition of material to support or strengthen the fractured or collapsed vertebral body. This procedure is generally referred to as Kyphoplasty and is generally described in U.S. Pat. No. 6,241,734.

One such treatment involves inserting a catheter having a balloon mounted on a distal end into an interior volume of a fractured vertebral body, wherein the interior volume has a relatively soft cancellous bone surrounded by fractured cortical bone. The balloon is expanded within the interior volume in an attempt to restore the vertebral body towards its original height. The balloon is deflated and removed from the interior volume, leaving a void within the vertebral body. PMMA or other bone filler material is injected through the cannula into the void to stabilize the vertebral body. The cannula is then removed and the cement cures to augment, fill, or fix the size and general shape of the vertebral body.

Another approach for treating VCF involves inserting an expandable mesh balloon into the targeted vertebral body. The balloon remains inside the vertebral body after it is inflated with PMMA or an allograft product, which limits intra-operative loss of height of the repositioned endplates.

It is desirable to provide an improved system, method and instruments for minimally invasively inserting a containment device such as, for example, an implant or a balloon, into an interior volume of a patient's bone.

BRIEF SUMMARY OF THE INVENTION

The present invention relates generally to a system, method and instrumentation for augmenting bones or other structures such as, for example, a vertebral body. More specifically, the present invention relates to an improved system and method for inserting a containment device, implant, balloon, etc. into an interior volume of a patient's vertebral body for the treatment of compressed bone voids, more specifically, vertebral compression fractures.

In a first preferred embodiment of the present invention, the system for accessing and inserting a containment device within an interior volume of a vertebral body includes an expandable containment, a chassis, a first guidewire, a working cannula, a second guidewire, a sleeve and a chassis. The expandable containment device preferably includes an outer surface encasing an interior cavity. The chassis preferably includes an interior cavity for at least partially enclosing the expandable containment device. The working cannula preferably includes a proximal end, a distal end and a hollow interior passageway extending from the proximal end to the distal end. The second guidewire preferably includes a partially flexible distal end portion such that the distal end portion can generally extend laterally across an anterior portion of the vertebral body in an insertion position. The sleeve preferably includes a proximal portion, a distal portion and a cannulated passageway extending from the proximal portion to the distal portion. The sleeve being sized and configured for insertion into the interior passageway of the working cannula. The distal portion of the sleeve being detachably coupled to the chassis while the proximal portion is preferably operatively associated with a bone filler injecting mechanism for introducing bone filler material through the cannulated passageway of the sleeve and into the interior cavity of the containment device.

The system preferably also includes a plunger including a partially flexible distal end portion and a cannulated bore so that the plunger can be advanced over the second guidewire.

The chassis preferably includes a leading end, a trailing end, an anterior portion and a posterior portion, the anterior portion including a window to enable and direct the outward expansion of the expandable containment device as the bone filler material is being introduced. The containment device preferably includes a plurality of anteriorly disposed cement-directing pores.

A preferred method for augmenting a vertebral body requires the steps of: (a) inserting a first guidewire into the interior of the vertebral body through one of a transverse process and a pedicle of the vertebral body; (b) advancing a working cannula over the first guidewire and into contact with the vertebral body; (c) removing the first guidewire from the vertebral body while retaining the position of the working cannula; (d) advancing a second guidewire through the working cannula and into the interior of the vertebral body, the second guidewire preferably assumes a curved configuration upon exiting a distal end of the working cannula so that a convex side of the second guidewire faces the anterior portion of the vertebral body and a concave side of the second guidewire faces the posterior portion of the vertebral body in an inserted configuration, advancement of the second guidewire into the interior of the vertebral body creates a curvilinear introductory pathway; (e) advancing a plunger through the working cannula and over the second guidewire to increase a dimension of the curvilinear introductory pathway created by the second guidewire, the plunger including a curved distal portion that is slidable through the working cannula and assumes a curved configuration upon exiting the distal end of the working cannula; (f) removing the plunger while retaining the positions of the second guidewire and the working cannula; (g) advancing a cannulated sleeve through the working cannula and along the second guidewire, the cannulated sleeve detachably coupled at a distal end thereof to a chassis, the chassis at least partially surrounding an expandable containment device, the chassis including an anteriorly facing window for directing the expansion of the expandable containment device; (h) introducing a bone cement through the cannulated sleeve and into the expandable containment device, thereby causing the expandable containment device to expand anteriorly out of the window formed in the chassis and to secrete a bolus of bone cement anteriorly with respect to the chassis; (i) uncoupling and removing the distal end of the cannulated sleeve from the proximal end of the chassis and (j) removing the second guidewire.

The bone cement introduction step preferably includes a two-step process wherein an amount of a lower viscosity cement is introduced followed by introducing an amount of a higher viscosity cement.

BRIEF DESCRIPTION OF THE SEVERAL VIEWS OF THE DRAWINGS

The foregoing summary, as well as the following detailed description of preferred embodiments of the augmentation and stabilization system, method and instrumentation of the present application, will be better understood when read in conjunction with the appended drawings. For the purposes of illustrating the minimally invasive spine augmentation and stabilization system, method and instrumentation of the present application, there is shown in the drawings preferred embodiments. It should be understood, however, that the application is not limited to the precise arrangements and instrumentalities shown. In the drawings:

FIGS. 1-13 illustrate various steps of practicing a preferred method of a minimally invasive spine augmentation and stabilization system of the present invention, with portions of a vertebra being generally transparent for clarity;

FIG. 14A illustrates a front perspective view of a chassis of the minimally invasive spine augmentation and stabilization system; and FIG. 14B illustrates a top plan, partial cross-sectional view of the chassis of FIG. 14A.

DETAILED DESCRIPTION OF THE INVENTION

Figure 1:
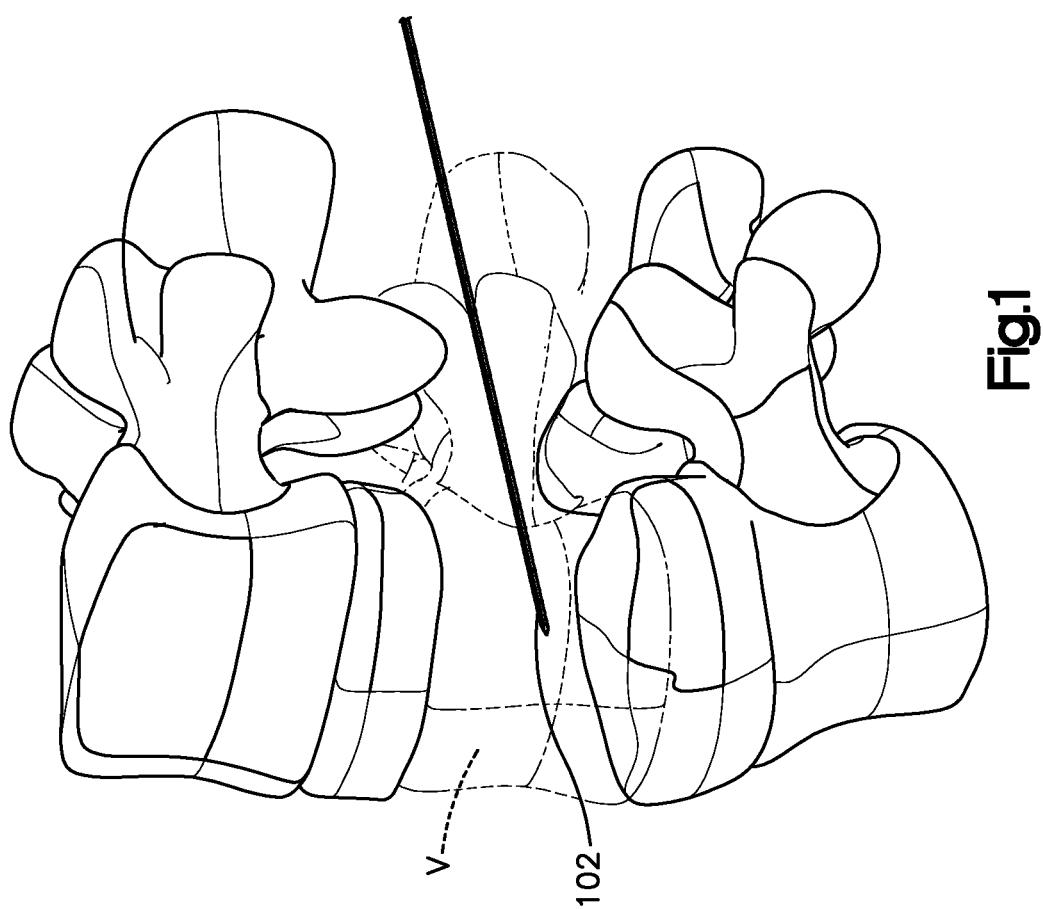

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the minimally invasive spine augmentation and stabilization system and related parts thereof. The words, "anterior", "posterior", "superior," "inferior", "medial", "lateral" and related words and/or phrases designate preferred positions and orientations in the human body to which reference is made and are not meant to be limiting. The terminology includes the above-listed words, derivatives thereof and words of similar import.

Certain exemplary embodiments will now be described with reference to the drawings. In general, such embodiments relate to a system, method and instrumentation for inserting an implant, containment device or balloon (collectively referred to herein as a containment device 125) within an interior volume of a vertebral body V. Once inserted, the containment device 125 preferably creates a cavity within the interior volume of the vertebral body V, restores the height of the vertebral body V, fills the cavity formed in the vertebral body V and stabilizes, aids and/or augments the patient's vertebral body V and spine. As generally understood by one of ordinary skill in the art, it should be understood that while the preferred containment device 125 will be described as and may generally be used in the spine (for example, in the lumbar, thoracic or cervical regions), those skilled in the art will appreciate that the containment device 125 may be used in other parts of the body such as, for example, long bones or bones in the hand, face, feet, extremities, cranium, or in nearly any bone in the human body.

Referring to FIGS. 10A-13 and as disclosed in International Patent Application No. PCT/US2008/083350 (published application No. WO 2009/064847), filed Nov. 13, 2008, titled "Porous Containment Device and Associated Method for Stabilization of Vertebral Compression Fractures, which claims priority to U.S. Provisional Patent Application No. 60/988,696, filed Nov. 16, 2007, titled "Porous Containment Devices and Associated Methods for Stabilization of Vertebral Compression Fractures," the entire contents of which are hereby incorporated by reference in their entirety, the system, method and instrumentation of the present invention is preferably used in conjunction with a porous or permeable containment device 125 for implantation into the interior volume of a targeted vertebral body V for use in restoring the anatomy of the targeted vertebral body V. The containment device 125 is expandable from an insertion configuration to an expanded configuration via, for example, a bone filler material such as, for example, a bone cement. Expansion of the containment device 125 by injection of the bone filler material preferably facilitates (i) cavity creation within the interior volume of the targeted vertebral body V, (ii) height restoration of the targeted vertebral body V, (iii) filling of the cavity formed in the interior volume of the targeted vertebral body V, and (iv) stabilization, aiding and/or augmentation of the targeted vertebral body V. The porous or permeable containment device 125 preferably enables (i) controlled bone cement outflow, (ii) increased contact surface with the surrounding cancellous bone and (iii) stabilization of the rotational and axial-translational movements of the porous containment device 125 with respect to the surrounding cancellous bone.

The containment device 125 may be formed from a compliant, semi-compliant or non-compliant material. The containment device 125 is preferably constructed from a PEEK material and is designed to have a pre-determined, specific shape when in the expanded configuration. More preferably, the containment device 125 has a dogbone-like or barbell-like shape in the expanded configuration to enhance stabilization with the surrounding cancellous bone. That is, the containment device 125, upon expansion or inflation, includes a leading end portion 125a, a trailing end portion 125b and a middle portion 125c therebetween such that the containment device 125 has first and second bulbous end portions and a comparatively narrow middle portion.

The containment device 125 preferably permits the bone filler material to flow out of or through the outer surface of the containment device 125. Preferably, the containment device 125 includes a plurality of holes or pores (not shown) formed in the outer surface for secreting the bone filler material. Preferably, the plurality of holes or pores are position in the anterior-facing surface of the middle portion 125c of the containment device 125 to direct the excretion of the bone filler material anteriorly out of the containment device 125 as the containment device 125 expands via injection of the bone filler material. The geometry of the containment device 125 in the expanded configuration serves as a barrier to confine the excreted bolus of bone filler material 130 anterior to the expanded containment device 125 and to limit bone filler material from flowing posteriorly or laterally with respect to the middle portion 125c of the containment device 125. The pores or holes may also incorporate a specifically designed shape and configuration to optimally meet the requirements of secreting the bone filler material, tissue infiltration and anchorage of the containment device 125 to the surrounding bone tissue.

Alternatively, the containment device 125 may include one or more flow-directing tentacles (not shown) extending from the outer surface or be formed at least partially from a permeable material, etc. to enable the bone filler material to be secreted from the containment device 125 to interdigitate with the surrounding bone tissue.

The containment device 125 may also include one or more knobs or ribs (not shown) to facilitate anchoring of the containment device 125 to the surrounding bone tissue, one or more air or fluid evacuation pores (not shown) to permit air or fluid from escaping from the interior volume of the containment device 125, and/or one or more radiopacity rings or markers (not shown) to enable a surgeon to locate and/or position the containment device 125 under X-ray imaging.

It should be understood that while the system, method and instrumentation of the present invention is preferably used in connection with the insertion of the containment device 125 disclosed in International Patent Application No. PCT/US2008/083350, the present invention is not so limited and may be used in conjunction with other now known or hereafter developed containment devices.

Referring to FIGS. 1-13, the system, method and instrumentation of a preferred embodiment for accessing and inserting the containment device 125 within the interior volume of a targeted collapsed, fractured, or otherwise damaged vertebral body V is illustrated. As generally understood by one of ordinary skill in the art, the targeted vertebral body V includes an anterior side, a posterior side, lateral sides therebetween, a superior portion, an inferior portion with a height therebetween, a spinous process, first and second transverse processes, and an intervertebral disc that is adhered both superiorly and inferiorly with respect to the damaged vertebral body V and which separates the damaged vertebral body V from adjacent vertebral bodies or vertebrae. The damaged vertebral body V is shown in a generally transparent configuration in FIGS. 1-13 to generally improve clarity of the components and steps of the preferred minimally invasive spine augmentation and stabilization system and method.

Referring to FIGS. 1-4B, the system and method preferably includes a rigid first guidewire 102, a working cannula 103 and a second guidewire 104. The first guidewire 102 may be a stylet, a K-wire, a guide pin, etc. The working cannula 103 preferably includes a proximal end (not shown), a distal end 103a and a hollow interior passageway (not shown) extending from the proximal end to the distal end 103a for enabling other instruments or elements to be advanced into the targeted vertebral body V. The second guidewire 104, which may also be in the form of a stylet, K-wire or guide pin, is designed and constructed so that at least a distal portion 104a thereof is at least partially flexible. In this manner, the second guidewire 104 includes a curved distal portion 104a. The curved distal portion 104a of the second guidewire 104 may be constructed by manufacturing the second guidewire 104 from a shape memory material so that the curved distal portion 104a of the second guide wire 104 can assume a straight configuration so that it can be inserted through the hollow interior passageway of the working cannula 103. Thereafter, at least the distal portion 104a of the second guidewire 104 reassumes, bends or curves upon exiting the distal end 103a of the working cannula 103.

It should be noted that the second guidewire 104 is not limited to being manufactured from a shape memory material and that the second guidewire 104 may be manufactured from any material as long as the distal portion 104a thereof is designed and constructed to have a curved or bent distal end such that the distal end 104a generally extends laterally across an anterior portion of the vertebral body V when the second guidewire 104 extends out of the cannula 103 in an insertion position.

Referring to FIGS. 5A and 5B, the system and method preferably also includes a hollow plunger or other cavity creation device 105 that is advanceable over the second guidewire 104 and into the vertebral body V. The plunger or other cavity creation device 105 is guided along the path created by the second guidewire 104. The plunger or other cavity creation device 105 assists in further creating or enlarging the introduction pathway for subsequently introduced elements of the system by creating a cavity along the exterior of the second guidewire 104 and thus enlarging the pathway created by the second guidewire 104. The exterior of the plunger 105 may include corrugation or other exterior surface features to assist in developing the pathway.

The hollow plunger or cavity creation device 105 is preferably at least partially flexible and includes a bendable or curveable distal portion 105a so that upon exiting the distal end 103a of the working cannula 103, the distal portion 105a of the plunger or cavity creation device 105 bends or curves to follow the path of the second guidewire 104. As with the second guidewire 104, the plunger or cavity creation device 105 may be manufactured from a shape memory material so that the distal portion 105a of the plunger or cavity creation device 105 initially assumes a straight configuration so that it can be inserted through the hollow interior passageway of the working cannula 103. Thereafter, at least the distal portion 105a of the plunger or cavity creation device 105 reassumes a distally bent or curved shape upon exiting the distal end 103a of the working cannula 103.

It should be noted that the plunger or cavity creation device 105 is not limited to being manufactured from a shape memory material and that the plunger or cavity creation device 105 may be manufactured from any material as long as the distal portion 105a thereof is designed and constructed to have a curved or bent distal end such that the distal end 105a is capable of bending or curving to follow the path of the second guidewire 104. For example, the plunger or cavity creation device 105 may be generally flexible to follow the path of the second guidewire 104 to direct the distal end 105a of the plunger or cavity creation device 105 along the path defined by the second guidewire 104 within the vertebral body V.

Referring to FIGS. 7A-14B, the system and method preferably also includes a cannulated sleeve 108, a containment device chassis 110 and the containment device 125. The cannulated sleeve 108 includes a proximal portion (not shown), a distal portion (not shown) and a interior passageway extending from the proximal portion to the distal portion. In use, the cannulated sleeve 108 is sized and configured to be inserted into the interior passageway of the working cannula 103. The distal portion of the cannulated sleeve 108 is preferably detachably coupled to the containment device chassis 110. The proximal portion is preferably coupleable with a mechanism such as, for example, a syringe (not shown) for introducing bone filler material or bone cement through the cannulated sleeve 108 and into the interior of the containment device 125, which is preferably housed inside of the chassis 110.

As best shown in FIGS. 14A and 14B, the chassis 110 includes a leading end 110a and a trailing end 110b wherein the leading end 110a may include a bullet nose tip or other taper for ease of advancement within the interior of the vertebral body V. As previously mentioned, the trailing end 110b is detachably coupled to the cannulated sleeve 108. The chassis 110 preferably also includes a hollow cavity 110c sized and configured to house or contain the containment device 125 when the containment device 125 is in the insertion configuration. An anterior portion of the chassis 110 preferably includes a window 111 to direct outward expansion of the containment device 125 upon inflation with the bone filler material or bone cement. The chassis 110 preferably has a curvature similar to the curvature of the distal end 104a of the second guidewire 104 and the distal end 105a of the plunger or cavity creation device 105. As such, the chassis 110 may be manufactured from a shape memory material so that the chassis 110 assumes the shape of the hollow interior passageway of the working cannula 103, as the chassis 110 is being inserted through the working cannula 103. Upon exiting the distal end 103a of the working cannula 103, the chassis 110 preferably reassume its curved shape.

It should be noted that the chassis 110 is not limited to being manufactured from a shape memory material and that the chassis 110 may be manufactured from any material as long as the chassis 110 is curveable or bendable to follow the path of the second guidewire 104. The chassis 110 is preferably formed from a material such as polyetheretherketone (PEEK), Nitinol, titanium, etc., but is not so limited. The posterior exterior or interior surface of the chassis 110 preferably includes a groove or slot 114 that is configured to mate with the second guide wire 104 such that the chassis 110 can be directed along the second guide wire 104 and into a desired position within the interior of the damaged vertebral body V.

The detachable coupling between the proximal end 110b of the chassis 110 and the distal end of the cannulated sleeve 108 may be by any mechanism now or hereafter known including, but not limited to, a friction fit, a press fit, or a force fit. In this manner, the cannulated sleeve 108 may be coupled to the chassis 110 by pressure and all forces can be transmitted by friction. In use, the chassis 110 can be decoupled from the cannulated sleeve 108 by holding the chassis 110 in place and pulling the cannulated sleeve 108 away from the chassis 110. Alternatively, the cannulated sleeve 108 may be coupled to the chassis 110 by a threaded connection, a bayonet coupling, or a plug-in connector such as by a pin formed in the cannulated sleeve 108 for engaging a slot formed in the chassis 110.

Alternatively, the cannulated sleeve 108 may be coupled to the chassis 110 via deformation of an elastic element (not shown). That is, the cannulated sleeve 108 may include an inner cannulated sleeve (not shown) and an outer cannulated sleeve (not shown) wherein the outer cannulated sleeve is movably associated with the inner cannulated sleeve. The elastic element may surround the inner cannulated sleeve, preferably adjacent the distal end thereof. The inner cannulated sleeve and elastic element are inserted into the chassis 110. Thereafter the outer cannulated sleeve is moved relative to the inner cannulated sleeve so that the distal end of the outer cannulated sleeve contacts the elastic element. Continued movement of the outer cannulated sleeve causes the elastic element to deform, resulting in the elastic element increasing in diameter which, in turn, causes the elastic element to press against the inner surface of the chassis 110.

Alternatively, the outer cannulated sleeve may be coupled to the elastic compression ring so that movement of the inner cannulated sleeve with respect to the outer cannulated sleeve causes the inner cannulated sleeve to contact and subsequently compress the elastic compression ring, which in turn causes the compression ring to expand and press against the chassis 110.

Furthermore, the cannulated sleeve 108 may be coupled to the chassis 110 by an intermediate clamping element (not shown). For example, the cannulated sleeve 108 may include an inner cannulated sleeve (not shown) and an outer cannulated sleeve (not shown) wherein the outer cannulated sleeve is movably associated with the inner cannulated sleeve. The intermediate clamping element may be formed on or coupled to the inner cannulated sleeve, preferably on the outer surface of the inner cannulated sleeve adjacent to a distal end thereof. The chassis 110 is thereafter placed between the inner cannulated sleeve and the intermediate clamping element. Thereafter movement of the outer cannulated sleeve with respect to the inner cannulated sleeve causes the outer cannulated sleeve to move over the intermediate clamping element thus securing the chassis 110. In addition, the cannulated sleeve 108 may be integrally formed with the chassis 110. The integrally formed cannulated sleeve 108 and implant chassis 110 may be separated by a predefined breaking region such that during the procedure the chassis 110 is separated from the cannulated sleeve 108 by rupturing the breaking region.

Figure 3:
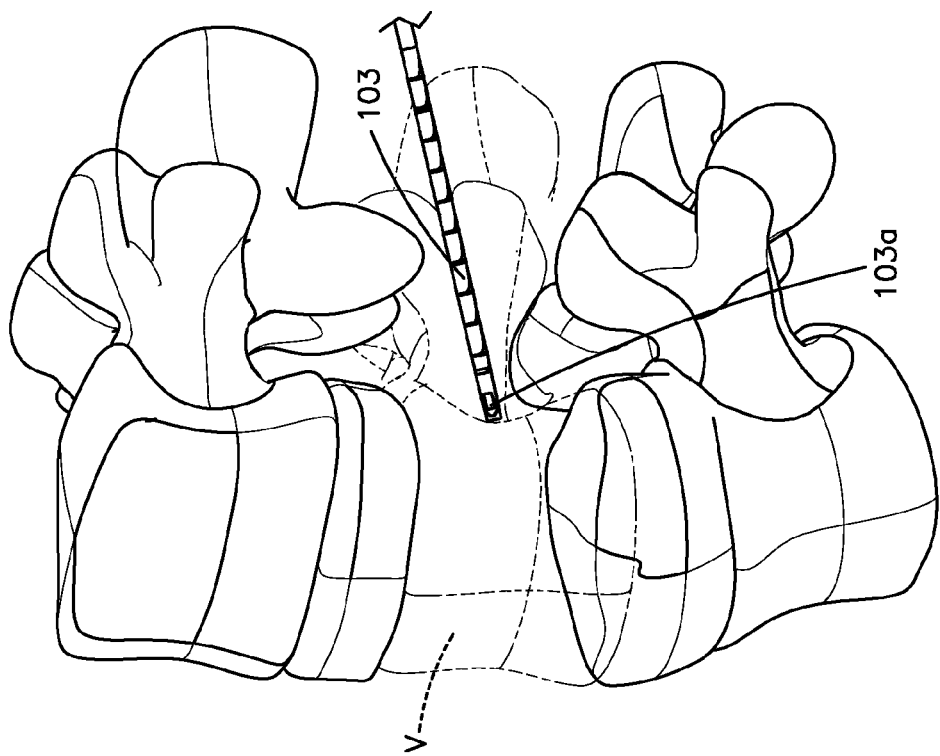
Figure 2:
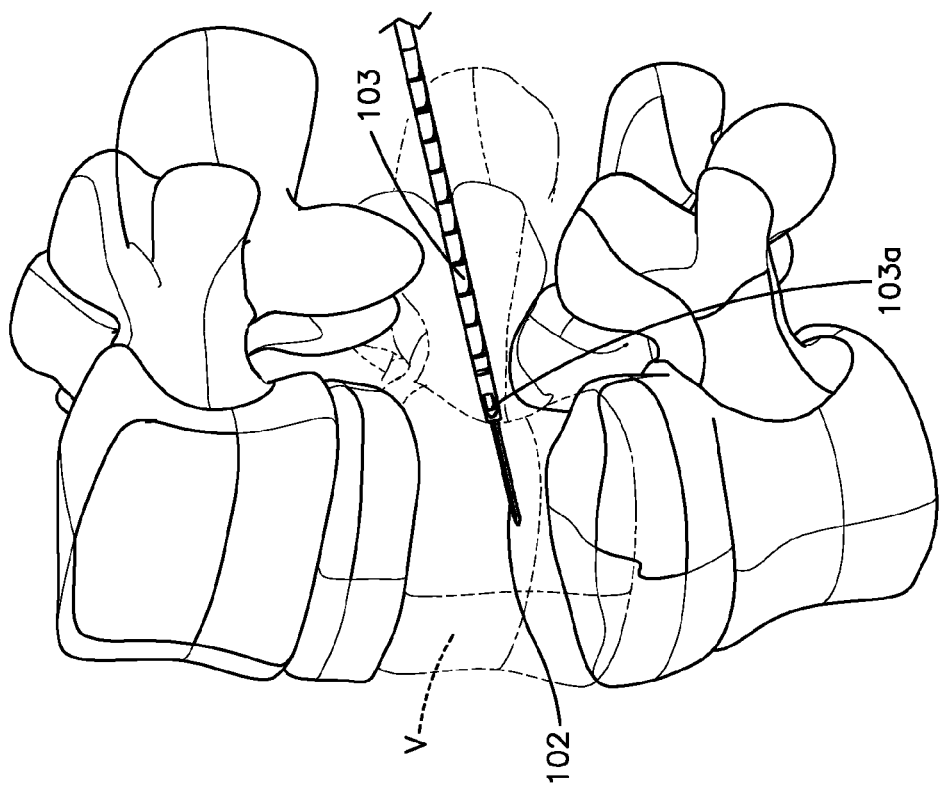
Figure 7B:
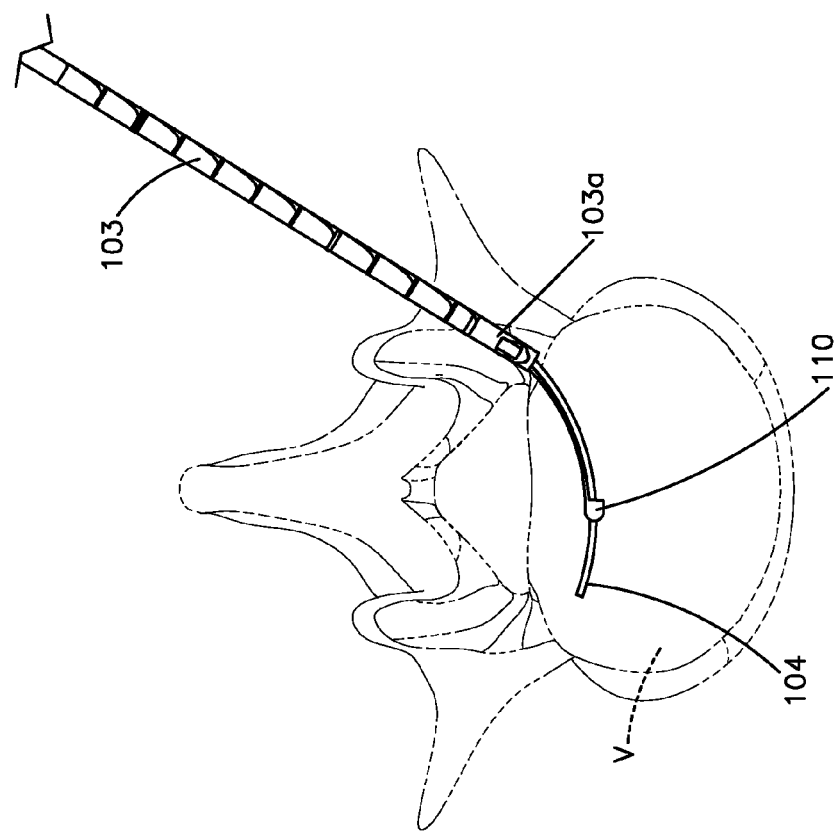
Figure 7A:
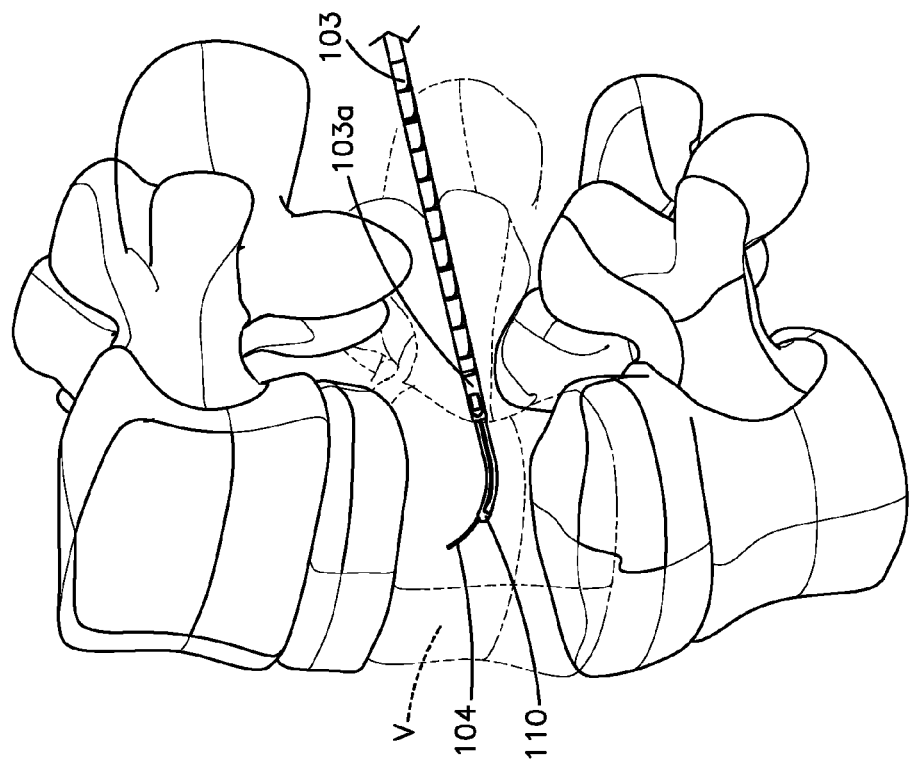

In continuing reference to FIGS. 1-13, a preferred method of inserting the containment device 125 within the interior volume of the targeted vertebral body V will now be described. After a damaged vertebral body V in need of repair is identified, the first guide wire 102 is introduced through the skin and musculature and into the interior volume of the targeted damaged vertebral body V, as illustrated in FIG. 1. The first guide wire 102 is introduced through a single transverse process or through one of the pedicles. Next, the working cannula 103 is introduced over the first guidewire 102 until the distal end 103a of the working cannula 103 is placed adjacent to an exterior of the targeted vertebral body V, as illustrated in FIG. 2. Alternatively, the distal end 103a of the working cannula 103 may be placed with the interior volume of the vertebral body V. The first guidewire 102 is then removed leaving the working cannula 103 in place, as illustrated in FIG. 3.

The second guidewire 104 is then introduced through the working cannula 103 and into the interior of the vertebral body V, as illustrated in FIGS. 4A and 4B. Upon exiting the distal end 103a of the working cannula 103, the second guidewire 104 curves or bends toward an opposite side of the vertebral body V as the second guidewire 104 is being introduced into the interior volume of the vertebral body V. As the second guidewire 104 curves or bends, the second guidewire 104 follows a path interior to the vertebral body V that has a concave side facing the posterior of the vertebral body V and a convex side facing the anterior of the vertebral body V. The distal end 104a of the second guidewire 104 is preferably position proximate the posterior wall of the vertebral body V. The insertion and positioning of the second guidewire 104 creates an introduction pathway for subsequently introduced elements of the system.

Once the second guidewire 104 is positioned within the interior volume of the vertebral body V, the plunger or cavity creation device 105 is introduced over the second guidewire 104. The plunger or cavity creation device 105 is directed along the path created by the second guidewire 104, as illustrated in FIGS. 5A and 5B. The plunger or cavity creation device 105 assists in further enlarging the introduction pathway for subsequently introduced elements of the system by creating a cavity along the exterior of the second guidewire 104 and thus enlarging the pathway created by the second guidewire 104. The exterior of the plunger 105 may include corrugation or other exterior surface features to assist in developing the pathway. The plunger 105 is then removed from the interior volume of the vertebral body V while retaining the second guidewire 104 and the working cannula 103 in place, as illustrated in FIGS. 6A and 6B.

Next, the cannulated sleeve 108, which includes the chassis 110 detachably coupled to the distal end thereof, is advanced through the working cannula 103 and into the interior volume of the vertebral body V along the introductory pathway created by the second guidewire 104 and the plunger or cavity creation device 105. The chassis 110 is inserted and travels over the second guidewire 104. To assist in this matter, the slot 114 formed on the interior or exterior posterior surface of the chassis 110 preferably interacts with the second guidewire 104 to steer the chassis 110 into position within the vertebral body V, as illustrated in FIGS. 7A-8B. The folded containment device 125 is protected from damage during insertion due to its partial enclosure by the chassis 110.

Alternatively, the containment device 125 may be introduced in a second step that occurs after positioning the chassis 110—filling and expansion of the containment device 125 is preformed as described below.

Referring to FIGS. 9A-11B, the containment device 125 is then expanded via introduction of the bone filler matter (e.g., bone cement). The introduction of bone cement is preferably performed via a two step process. That is, a low viscosity bone cement is injected through the cannulated sleeve 108 and into the containment device 125 causing the containment device 125 to unfold and partially expand anteriorly out of the anterior window 111 formed in the chassis 110. In addition, a small amount of bone cement is secreted through the pores toward the anterior portion of the vertebral body V. Secretion of the bone cement through the pores preferably forms the cement bolus 130. Next, a higher viscosity bone cement is then preferably injected through the cannulated sleeve 108 and into the containment device 125 to further expand the containment device 125. Moreover, additional bone cement is secreted through the pores formed in the containment device 125. In addition, injection of the higher viscosity bone cement preferably restores the height of the vertebral body V. The outflow of bone cement through the pores, resulting in the cement bolus 130, is preferably directed anteriorly to limit posterior or lateral cement flow within the vertebral body V. The posterior and lateral cement flow is limited by the barrier formed by the geometry of the expanded containment device 125 and the chassis 110.

The secreted bone cement 130 preferably provides interdigitation and stabilization to limit slippage between the containment device 125 and the surrounding bone tissue interior to the vertebral body V. In addition, the bone cement injected into the containment device 125 provides height restoration and conservation of the spacing between the endplates of the vertebral body V. The barrier to posterior cement flow within the vertebral body V that is provided by the geometry of the expanded containment device 125 and the chassis 110 limits the bone cement from leaking through any fracture lines inherent on the posterior wall of the vertebral body V, a condition noted in about forty percent (40%) of all vertebral body fracture cases.

It should be understood that while the preferred method uses a two-step process for injecting the bone cement, the system and method is not so limited and the containment device 125 may be inflated using a single-step process or a process involving more than two steps.

Figure 13:
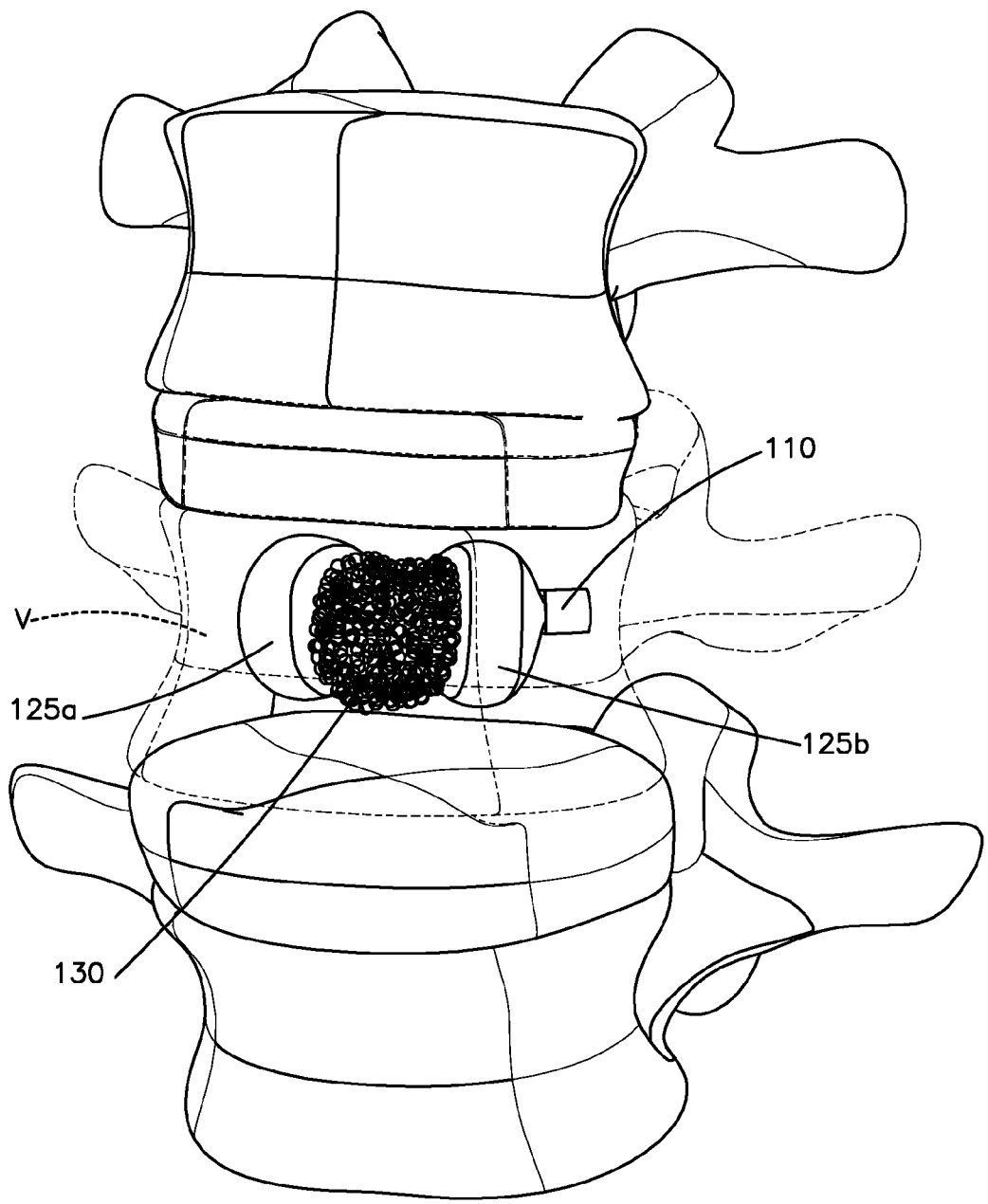

The introduction of the containment device 125 through a single transverse process or pedicle and the elongated curved or bent geometry of the second guidewire 104 permits a less invasive procedure than a bi-pedicular or bi-transverse process approach in which a pair of devices or implants are introduced into the interior of the vertebral body V. Upon desired expansion of the containment device 125 and creation of the cement bolus 130, the chassis 110 is uncoupled from the distal end of the cannulated sleeve 108 by actuating or employing any of the above described appropriate detachment mechanisms, depending on the particular mechanism chosen for the system, at which point the cannulated sleeve 108 is removed from the working cannula 103. The working cannula 103 and the second guidewire 104 are preferably removed from the patient's body, as illustrated in FIGS. 12A-13, while leaving the containment device 125 and chassis 110, as well as the cement bolus 130, within the interior of the vertebral body V. Alternatively, the containment device 125 may be partially or fully removed from the vertebral body V by creating weakened portions in the containment device 125 along which the containment device 125 may tear to permit at least partial removal of the containment device 125 from the vertebral body V.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the present description.

We claim:

1. A system configured to augment a vertebral body, the system comprising:
   an expandable containment device that defines an interior device cavity, and further defines a leading end with respect to a direction of insertion of the expandable containment device into the vertebral body, and a trailing end that is opposite the leading end and spaced from the leading end substantially along a first direction;
   a chassis that defines an interior chassis cavity that is configured to at least partially receive the expandable containment device;
   a cannula that defines a proximal cannula end, a distal cannula end opposite the proximal cannula end, and a cannula passageway that extends between the proximal cannula end and the distal cannula end;
   a guidewire sized to be received in the cannula passageway and having distal guidewire end portion, wherein moving the distal guidewire end portion from inside the cannula to outside the cannula causes the distal guidewire end portion to change shape such that the distal guidewire end portion generally extends laterally across the vertebral body when the distal guidewire end portion is disposed inside the vertebral body; and a sleeve that defines a sleeve passageway, the sleeve sized and configured to be inserted into the cannula passageway, the sleeve configured to be detachably coupled to the chassis such that filler material can be introduced through the sleeve passageway-and into the interior device cavity to expand the expandable containment device along a second direction that is substantially perpendicular to the first direction when the expandable containment device is at least partially disposed in the interior chassis cavity, thereby causing at least a portion of the expandable containment device to be outwardly disposed with respect to the chassis along the second direction.

2. The system of claim 1, further comprising a plunger, the plunger including at least a partially flexible distal end portion and a bore so that the plunger can be advanced over the guidewire.

3. The system of claim 1, wherein the chassis includes an anterior portion and a posterior portion opposite the anterior portion, the anterior portion defining a window that exposes a portion of the expandable containment device such that the expandable containment device expands toward an anterior portion of the vertebral body when filler material is introduced into the interior device cavity and the expandable containment device and the chassis are disposed inside the vertebral body.

4. The system of claim 1, wherein the chassis defines a leading end and a trailing end opposite the trailing end, and the leading end of the chassis includes a taper nose.

5. The system of claim 3, wherein the chassis has a curvature similar to a curvature of the distal guidewire end portion when the distal guidewire end portion is disposed outside the cannula.

6. The system of claim 1, wherein the expandable containment device includes a first end portion, a second end portion opposite the first end portion, and a middle portion that is disposed between the first and second end portions, the middle portion having a circumference smaller than a circumference of either end portion.

7. The system of claim 6, wherein at least a portion of the middle portion of the containment device includes a plurality of anteriorly disposed cement-directing pores.

8. The system of claim 1, wherein the guidewire comprises a shape memory material.

9. The system of claim 1, wherein the distal guidewire end portion has a first shape and a second shape that is different from the first shape, and moving the distal guidewire end portion from inside the cannula to outside the cannula causes the distal guidewire end portion to transition from the first shape to the second shape.

10. The system of claim 9, wherein the first shape is a substantially straight shape, the second shape is a curved shape, and, in the curved shape, the distal guidewire end portion defines a convex side that faces an anterior portion of the vertebral body when the distal guidewire end portion is disposed outside the cannula and inside the vertebral body.

11. The system of claim 10, wherein, in the curved configuration, the distal guidewire end portion defines a convex side that faces a posterior portion of the vertebral body when the distal guidewire end portion is disposed outside the cannula and inside the vertebral body.

12. The system of claim 1, wherein the chassis is configured to remain stationary relative to the expandable containment device while the expandable containment material is expanding due to the introduction of filler material in the interior device cavity.

13. The system of claim 1, wherein the guidewire is a second guidewire, the system further comprising a first guidewire that is configured to extend into the vertebral body, and the first guidewire is configured to be received in the cannula passageway as the cannula moves along the first guidewire until the distal cannula end is disposed adjacent the vertebral body.

14. The system of claim 1, wherein the first guidewire is removable from the cannula passageway and the second guidewire is subsequently insertable through the cannula passageway and into the vertebral body.

15. The system of claim 1, wherein the expandable containment device is coupled to the chassis so that the chassis and the expandable containment device can be introduced simultaneously into the vertebral body.

16. The system of claim 4, wherein the expandable containment device is configured to be coupled to the chassis so that the at least a portion of the expandable containment device is disposed between the leading and trailing ends of the chassis once the chassis is disposed inside the vertebral body.

17. A system configured to augment a vertebral body, the system comprising:
an expandable containment device that defines an interior device cavity;
a cannula that defines a proximal cannula end, a distal cannula end spaced from the proximal cannula end, and a cannula passageway that extends between the proximal cannula end and the distal cannula end;
a chassis that defines an interior chassis cavity that is configured to at least partially receive the expandable containment device, the chassis configured to be received in the cannula passageway, the chassis defining an insertion end and a trailing end opposite the leading end, the chassis extending along a chassis axis, the chassis having a first shape and a second shape that is different from the first shape, wherein moving the chassis from inside the cannula to outside the cannula causes the chassis to transition from the first shape to the second shape such that the chassis is curved along the chassis axis; and
a sleeve that defines a sleeve passageway, the sleeve sized to be received in the cannula passageway, the sleeve configured to be detachably coupled to the chassis such that filler material can be introduced through the sleeve passageway and into the interior device cavity to expand the expandable containment device when the expandable containment device is at least partially disposed in the interior chassis cavity.

18. The system of claim 17, wherein the first shape is a shape substantially similar to a shape of the cannula passageway, and the second shape is defined as when the chassis is curved along the chassis axis.

19. The system of claim 17, wherein the chassis comprises shape-memory material.

20. The system of claim 17, wherein the chassis includes an anterior portion, a posterior portion opposite the anterior portion, the posterior and anterior portions cooperate so as to at least partially define the interior chassis cavity, the anterior portion defines a window that leads to the interior chassis cavity, and the window exposes a portion of the expandable containment device such that introduction of filler material into the interior device cavity causes the portion of the expandable containment device to expand toward an anterior portion of the vertebral body when the chassis is disposed inside the vertebral body.

21. The system of claim 16, wherein moving the chassis from inside the cannula to outside the cannula causes the chassis to bias into the second shape such that the chassis curves along the chassis axis.

22. A system configured to augment a vertebral body, the system comprising:
- an expandable containment device that defines an interior device cavity;
- a cannula that defines a proximal cannula end, a distal cannula end spaced from the proximal cannula end along an insertion direction, and a cannula passageway that extends between the proximal cannula end and the distal cannula end;
- a chassis that defines an interior chassis cavity that is configured to at least partially receive the expandable containment device, the chassis configured to be received in the cannula passageway, the chassis having a first shape and a second shape that is different from the first shape, wherein moving the chassis from inside the cannula to outside the cannula causes the chassis to transition from the first shape to the second shape such that the chassis curves so as to extend laterally with respect to the insertion direction; and
- a sleeve that defines a sleeve passageway, the sleeve sized to be received in the cannula passageway, the sleeve configured to be detachably coupled to the chassis such that filler material can be introduced through the sleeve passageway and into the interior device cavity to expand the expandable containment device when the expandable containment device is at least partially disposed in the interior chassis cavity.

23. The system of claim 22, wherein moving the chassis from inside the cannula to outside the cannula causes the chassis to bias into the second shape.

24. The system of claim 22, further comprising a guidewire sized to be received in the cannula passageway and having distal guidewire end portion, wherein moving the distal guidewire end portion from inside the cannula to outside the cannula causes the distal guidewire end portion to change shape such that the distal guidewire end portion generally extends laterally with respect to the insertion direction when the distal guidewire end portion is disposed outside the cannula.

25. The system of claim 22, wherein the chassis includes an anterior portion, a posterior portion opposite the anterior portion, the posterior and anterior portions cooperate so as to at least partially define the interior chassis cavity, the anterior portion defines a window that leads to the interior chassis cavity, and the window exposes a portion of the expandable containment device such that introduction of filler material into the interior device cavity causes the portion of the expandable containment device to expand toward an anterior portion of the vertebral body when the chassis is disposed inside the vertebral body.

26. The system of claim 22, wherein the expandable containment device is coupled to the chassis so that the chassis and the expandable containment device can be introduced simultaneously into the vertebral body.

27. The system of claim 22, wherein the chassis comprises shape-memory material.

* * * * *